United States Patent [19]

Dedieu et al.

[11] Patent Number: 5,344,971
[45] Date of Patent: Sep. 6, 1994

[54] PROCESS FOR DEODORIZING A MERCAPTO ACID BY EXTRACTING MALODOROUS COMPOUND THEREFROM WITH A SUPERCRITICAL FLUID

[75] Inventors: Michel Dedieu, Maisons Laffitte; Hervé Burgaud, Dammartin En Goele; Eric Lapoirie, Villemomble; Véronique Gurfein, Le Plessis Robinson; Gérard Malle, Villiers-Sur-Morin, all of France

[73] Assignee: L'Oreal, Paris, France

[21] Appl. No.: 45,095

[22] Filed: Apr. 12, 1993

[30] Foreign Application Priority Data

Oct. 15, 1992 [FR] France .................. 92 12344

[51] Int. Cl.$^5$ ............ C07C 53/00; C07C 55/02; C07C 323/52
[52] U.S. Cl. ............................ 562/512; 562/593
[58] Field of Search ........................ 562/512, 593

[56] References Cited

U.S. PATENT DOCUMENTS

| | | | |
|---|---|---|---|
| 3,193,463 | 7/1965 | Schweizer | 167/87.1 |
| 3,860,641 | 1/1975 | Zengel et al. | 562/512 |
| 4,250,331 | 2/1981 | Shimshick | 562/485 |
| 4,322,550 | 3/1982 | Kimble | 562/512 |
| 5,008,432 | 4/1991 | Roberts | 558/436 |
| 5,023,371 | 6/1991 | Tsui et al. | 562/512 |
| 5,057,622 | 10/1991 | Chisholm et al. | 560/152 |
| 5,157,147 | 10/1992 | Chisholm et al. | 560/147 |

OTHER PUBLICATIONS

Patent Abstracts of Japan, vol. 8, No. 114 (C=225) May 26, 1984 & JP-A-57 027 866 (Raison) Feb. 14, 1984.
Angewandte Chemie, International Edition in English, vol. 17, No. 10, Oct. 1978, Weinhem, DE, pp. 710-715, P. Hubert et al.
Food Technology, vol. 42, No. 6, Jun. 1988, pp. 145-150, F. Temelli et al.
Cosmetics and Toiletries, vol. 106, No. 8, Aug. 1991, pp. 61-67, J. W. King.

*Primary Examiner*—José G. Dees
*Assistant Examiner*—Barbara S. Frazier
*Attorney, Agent, or Firm*—Cushman, Darby & Cushman

[57] ABSTRACT

A process for deodorizing a mercapto acid includes extracting malodorous compounds present therein by treating the mercapto acid in the presence of a polar solvent with a supercritical extraction fluid having a critical temperature ranging from 0° to 135° C. and a critical pressure ranging from $10^6$ to $10^7$ Pascals. The mercapto acid has the formula HS—A—COOH wherein A represents

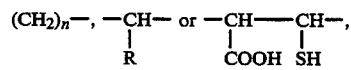

wherein n is an integer ranging from 1 to 4 and R is a linear or branched $C_1$-$C_3$ alkyl.

17 Claims, 1 Drawing Sheet

PROCESS FOR DEODORIZING A MERCAPTO ACID BY EXTRACTING MALODOROUS COMPOUND THEREFROM WITH A SUPERCRITICAL FLUID

The present invention relates to a process for deodorizing a mercapto acid and to the deodorized product thereby obtained.

BACKGROUND OF THE INVENTION

Mercapto acids are well-known derivatives which have a thiol (—SH) function and an acid (—COOH) function. They have many applications. Thioglycolic (or mercaptoacetic) acid, for example, may be used in its acid form as an intermediate in the synthesis of many pesticides and pharmaceutical products, or in its acid or salified (especially ammonium, amine, sodium, potassium or calcium salt) form for the pickling of metal surfaces, the treatment of sulphide ores and the treatment of leathers and hides; in the cosmetics industry, it also constitutes the most widely used reducing agent for the permanent-reshaping of hair (curling or straightening) and the main active substance in depilatory milks and creams. Similarly, thiolactic acid (2-mercaptopropionic acid) is used as a reducing agent for the permanent-reshaping of hair or as a constituent of depilatory milks and creams.

Pure mercapto acids have a slight pungent odor which is not really unpleasant. However, they always contain, in practice, sulphide compounds such as hydrogen sulphide and low molecular weight mercaptans, especially methanethiol or ethanethiol, which have an especially unpleasant nauseating odor. Very small amounts of these sulphide compounds are sufficient for their presence to be detected using one's sense of smell, the nose being, in this case, the best instrument of detection.

The presence of these malodorous compounds is associated with various processes of decomposition of the mercapto acids, which processes are still very poorly understood but are doubtless due to both ionic and free-radical mechanisms that can take place when air is absent. This decomposition and the resulting formation of malodorous compounds can, moreover, be monitored over time by various analytical techniques, especially by the so-called headspace method in gas chromatography.

In the various applications of mercapto acids, and more especially in their cosmetic applications, the odor emitted by the products employed constitutes a genuine nuisance to the users. An effort has hence been made to mask the odor of mercapto acids by perfumes, but this odor is, in general, too powerful to be amenable to satisfactory masking.

The proposal has also been made, in Japanese Patent Application No. 82-136,280 published under No. 84/027,866, to deodorize thioglycolic acid, pure or mixed with water, by extraction with a $C_4$-$C_8$ non-aromatic hydrocarbon. However, it was found that, while this extraction process enables the malodorous compounds to be extracted and a deodorized acid to be obtained, the deodorization effect obtained is not lasting with the passage of time, since the malodorous compounds quickly re-form and cancel out the benefit obtained by the treatment; in some cases, the odor even returns at a higher level than the initial level.

Moreover, it is known to use supercritical fluids as extraction fluids. Supercritical fluids are phases which are at a higher temperature and pressure than critical values characteristic of the compound in question; in the supercritical region, there is no liquid/gas equilibrium curve separating a region in which the compound might be gaseous from a region in which it might be liquid. Extraction with a supercritical fluid affords many advantages; this is especially true when carbon dioxide is used; there is no contamination with a residual solvent; the critical temperature of $CO_2$ is close to room temperature, enabling extraction to be performed under mild conditions and in a non-oxidizing environment; and $CO_2$ is a non-inflammable and non-toxic liquid. Such extraction processes are, for example, described in P. HUBERT and O. G. VITZHUM Angew. Chem. Int. Ed. Engl 17, 710–715 (1978); F. TEMELLI et al, Food Techn. 42 (6) 145–150 (1988); D. A. MOYLER Supercritical fluids for extract preparation in Distilled Beverage Flavor—Recent developments, J. R. PIGOTT and A. PATERSON, Chichester Editions, England, Ellis HORWOOD Ltd (1989); J. W. KING, Cosmetic and Toiletries, 106 (8) 61–67 (1991). In all these processes, a gaseous extract containing the desired substance and a liquid extraction residue, which can be discarded, are obtained. Furthermore, as noted in the J. W. KING paper cited above, the treated products are non-polar compounds, similar to lipids and very hydrophobic.

The present invention relates to a process for deodorizing mercapto acids by extraction using a supercritical fluid; such a process enables a lastingly deodorized product to be obtained.

SUMMARY

The subject of the present invention is hence a process for deodorizing a mercapto acid using an extraction fluid, this process consisting in separating and extracting with the said fluid the greater part of the malodorous decomposition products contained in the mercapto acid subjected to the treatment, characterized in that the mercapto acid is of the formula:

$$HS-A-COOH \quad \quad (I)$$

in which formula A represents
the divalent radical:

where n is an integer between 1 and 4;
the divalent radical

where R represents a linear or branched $C_1$-$C_3$ alkyl radical; or
the divalent radical:

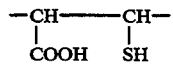

and in that the extraction fluid is a supercritical fluid consisting of a compound whose critical temperature is between 0° and 135° C. and critical pressure between $10^6$ and $10^7$ pascals, the process being carried out in the presence of at least one polar solvent for the mercapto acid.

The compound in the state of supercritical fluid which is preferably used is carbon dioxide ($CO_2$).

The mercapto acid treated is preferably thioglycolic acid or thiolactic acid; 4-mercaptobutyric acid, 3-mercaptopropionic acid and dimercaptosuccinic acid may, however, also be mentioned.

The polar solvent is preferably chosen from the group composed of water, linear or branched $C_1-C_5$ monohydric alcohols, $C_2-C_6$ diols, $C_3-C_6$ polyols and mixtures thereof.

The monohydric alcohol may be chosen from the group composed of methanol, ethanol, 1-propanol, 2-propanol, 1-butanol, 2-butanol, 2-methylpropanol and 1-pentanol.

The diol is advantageously chosen from the group composed of ethylene glycol, 1,2-propanediol, 1,3-propanediol, 1,3-butanediol, 2,3-butanediol, 1,5-pentanediol and 1,6-hexanediol.

The polyol can advantageously be glycerol.

Water is the preferred solvent since, in most applications of the mercaptide undergoing treatment, its subsequent removal is not necessary.

The presence of a solvent for performing the extraction is necessary. In effect, tests showed that the mercapto acids of formula (I), and especially thioglycolic acid, were miscible in all proportions with a supercritical fluid, and especially with supercritical $CO_2$, the mixture displaying no discontinuity: hence only a single phase forms, and it is not possible to perform an extraction. This logically led a person skilled in the art to rule out any treatment with supercritical fluid for the deodorization of mercapto acids. According to the present invention, it was found that, by introducing a polar solvent into the extraction medium, a miscibility gap is produced, with formation of at least two phases; the malodorous compounds in the mercapto acid are extracted with the supercritical fluid and, when the pressure of the extraction medium is lowered, they are carried away with the extraction fluid; the residue consists of a solution of mercapto acid in the polar solvent used.

The process according to the invention hence makes it possible to obtain a mercapto acid which is deodorized and which has its distinctive slightly pungent odor. The fact that it is deodorized does not necessarily mean that it is pure; in effect, it could contain odorless impurities. Furthermore, quite unexpectedly, it was found that, after at least two months of storage of the solution of mercapto acid at room temperature and protected from aerial oxygen, it is not possible to detect the presence of malodorous compounds using one's sense of smell. Consequently, they are not re-formed, or are re-formed only in very small proportions, since they are not detected by the nose.

The solvent is used in amounts of between 1 and 99% by weight relative to the mercapto acid. It may be added either to the mercapto acid or to the supercritical fluid used. The amount of solvent which can be introduced is limited by the maximum solubility of the said solvent in the mercapto acid and in the extraction fluid.

When the supercritical fluid is carbon dioxide, it is preferable to use an aqueous solution of mercapto acid having a concentration of between 0.1 mol per liter and 14 mol per liter, and preferably between 1 mol per liter and 10 mol per liter.

According to the invention, the efficiency of the extraction with respect to the amount of supercritical fluid employed may be improved by performing the said extraction in the presence of an inert gas such as helium, nitrogen or argon; this inert gas may be introduced into the extraction medium separately or in the form of a mixture with the supercritical fluid.

According to the invention, the extraction may be performed either in continuous, in semi-continuous or in discontinuous fashion.

When the procedure is carried out in discontinuous fashion, the mercapto acid, the polar solvent, the extraction fluid and, where appropriate, the inert gas are introduced into the reactor, and it is arranged for the critical pressure and temperature conditions to be obtained in the closed reactor. The products are left in contact, preferably with stirring, for a cycle lasting between 5 and 30 minutes, during which the supercritical fluid becomes loaded with malodorous compounds; the extraction fluid is then removed by decompression. One or more cycles are performed, where appropriate, under the same conditions, and a solution of deodorized mercapto acid is collected.

When the procedure is carried out in semi-continuous fashion, the mercapto acid and the polar solvent are introduced, the reactor is filled with extraction fluid and the pressure and temperature in the reactor are taken to values above the critical pressure and temperature. A washing flow with the supercritical fluid is then established for a specified period, which flow may be constant or variable, this flow being dependent on the installation. In the case of supercritical $CO_2$ it is generally at between 0.5 and 3 kg/hour; it is, however, preferable to relate this flow to the amount of the (mercapto acid/solvent) mixture. In the case of thioglycolic acid in aqueous solution and supercritical $CO_2$, the flow of carbon dioxide is at between 1 and 30 kg/hour per kg of (thioglycolic acid/solvent) mixture. Finally, the flow of supercritical fluid is stopped and the solution of mercapto acid is collected.

When the procedure is carried out in continuous fashion, the extraction of the (mercapto acid/solvent) mixture is performed with a supercritical fluid employing parallel-flow or countercurrent operation on a separating column. A continuous flow of both the mixture to be extracted and the supercritical fluid is established. The ratio of the two flows is fixed in accordance with the efficiency of separation which is desired.

After separation of the carbon dioxide, the deodorized liquid residue collected consists of the mercapto acid and the greater part of the solvent; it possibly contains small amounts of extraction fluid, for example $CO_2$. The solution of deodorized mercapto acid obtained is preferably packaged carefully, protected from aerial oxygen, in a container known for its chemical compatibility with the mercapto acid, where appropriate without removing the residual extraction fluid, for example $CO_2$.

The solvent can, however, be removed by any known process before storage, especially when the solvent is other than water.

Irrespective of the extraction process used, the extraction fluid may be recycled after being relieved of the extracted compounds by purification according to known methods such as passage through a bed of active charcoal.

The subject of the present invention is also the deodorized product obtained by the process of the present invention.

The solutions of deodorized mercapto acid of formula (I) may be used in all industrial applications known for these products. The mercapto acid is generally combined with other ingredients in a composition whose formulation varies according to the application. The efficiency of the deodorization enables them to be used, without imparting an unpleasant odor, in any composition which must not have an unpleasant odor and whose other ingredients do not possess an unpleasant odor. There may be mentioned, as an example, the possibility of combination with thiols such as cystsine or cysteamine which do not have an unpleasant odor.

When the composition used contains ingredients that are liable to cause the benefit of the deodorization to be lost by inducing the formation of malodorous compounds, it can be advantageous to package the solution of mercapto acid obtained separately, and to prepare the amount of composition needed for the application at the last moment.

The examples given below, as an illustration and without implied limitation, will enable a better understanding of the invention to be gained.

Examples 1 to 6 illustrate the deodorization process according to the invention.

DETAILED DESCRIPTION

Figure 1:
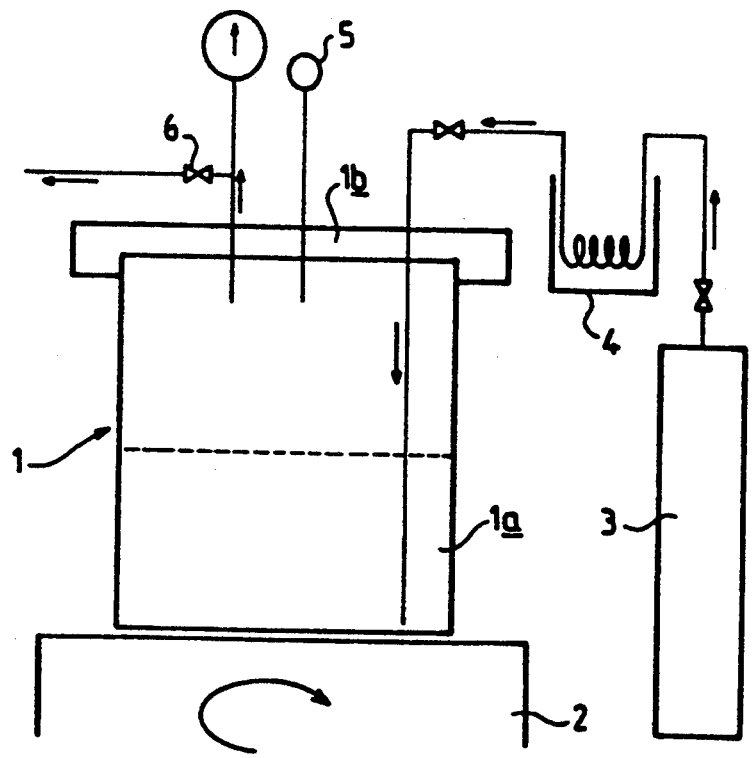
FIG. 1 is a flow diagram of a discontinuous process according to the invention.

The experiments of Examples 1 to 3 were performed in an extraction reactor operating in discontinuous fashion, shown diagrammatically in FIG. 1. The installation contains a reactor 1 consisting of a pressure-resistant steel casing 1a and a lid 1b. The reactor 1 is equipped with a stirring and heating system shown diagrammatically at 2. The extraction fluid is stored under pressure in a reservoir 3; it is dispatched to the reactor 1 via a condenser 4, so as to effect filling of the reactor with an extraction fluid in the liquid state. The reactor 1 is equipped with a safety valve 5. It is connected via a valve 6 to a restrictor (not shown) which effects slow decompression of the reactor.

EXAMPLE 1

35 ml of an aqueous solution of thioglycolic acid containing 92 g/l (1M) are introduced into the reactor 1, which has a capacity of 100 ml. The reactor is then filled with liquid carbon dioxide at 8° C. from a reservoir 3 consisting of a $CO_2$ bottle at 60 bars and 20° C. After the reactor 1 has been isolated, its contents are brought to 60° C. The pressure observed is $145 \times 10^5$ pascals. The contents of the reactor 1 are left stirring for 20 minutes. The valve 6, which discharges the flow into a restrictor consisting of a tube 30 cm in length and 50 μm in internal diameter, is then opened. When the pressure reaches 50 bars, the apparatus is cooled to 8° C. and bled, and a second cycle identical to that just described is performed.

The aqueous solution of thioglycolic acid obtained, which no longer possesses the initial nauseating odor of the compound, but a slight pungent odor, is drawn off.

EXAMPLE 2

50 ml of aqueous solution of thioglycolic acid containing 368 g/l (4M) are introduced into the reactor 1. The reactor is filled with liquid $CO_2$ at 60 bars and 15° C., and its contents are heated to 41° C. until the pressure reaches $110 \times 10^5$ pascals. The contact time is 15 minutes. Two successive cycles are performed.

The solution of thioglycolic acid obtained no longer has a nauseating odor.

EXAMPLE 3

Two extraction cycles are performed as in Example 1 on 50 ml of an aqueous solution of thioglycolic acid containing 92 g/l (1M). Liquid carbon dioxide is introduced at 60 bars and 20° C., and the contents of the reactor are then brought to 35° C., the pressure being adjusted to $130 \times 10^5$ pascals using gaseous helium.

The aqueous solution of thioglycolic acid collected no longer has a nauseating odor.

Figure 2:
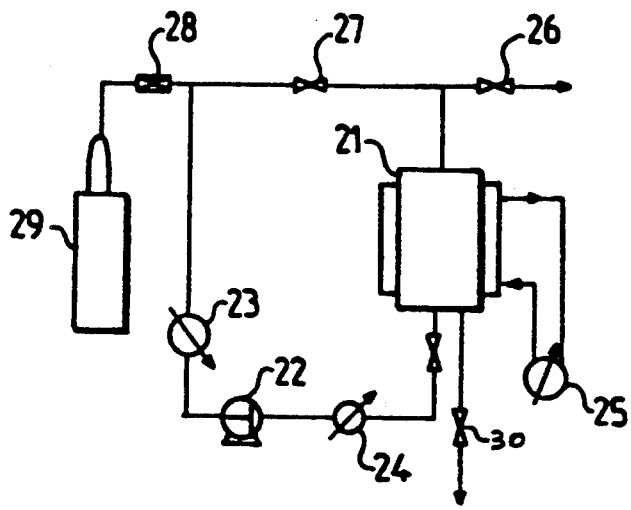
FIG. 2 is a flow diagram of a semi-continuous process according to the invention.

Examples 4 to 6 given below were performed in semi-continuous fashion in the installation shown diagrammatically in FIG. 2. This installation contains an autoclave 21 fed by a pump 22 for circulation and pressurization of the extraction fluid. Upstream of the pump 22, a condenser 23 for liquefying the extraction fluid is arranged. Downstream of the pump 22, a heat exchanger 24 is provided in order to bring the extraction fluid to the temperature conditions for the extraction. A heat exchanger 25 enables the temperature of the autoclave to be regulated. On emerging from the autoclave 21, the flow of material is partially drawn off via the micrometer valve 26 and partially recycled via the micrometer valve 27, the relative adjustment of these two valves effecting the regulation of the extraction pressure. The feed of extraction fluid is effected, via a non-return valve 28, from a container 29 towards the condenser 23. Draining of the autoclave 21 takes place via the valve 30.

EXAMPLE 4

The autoclave 21 is charged with 100 ml of an aqueous solution of thioglycolic acid containing 184 g/l (2M). After the whole of the installation has been pressurized with liquid $CO_2$, a flow of supercritical $CO_2$ is established by means of the pump 22 under the following extraction conditions:
pressure: $250 \times 10^5$ pascals
temperature: 40° C.
circulation flow rate: 2.4 kg/h
The extraction time is fixed at 20 minutes. After decompression and draining of the autoclave 21, the solution of thioglycolic acid no longer has the initial unpleasant odor.

EXAMPLE 5

The autoclave 21 is charged with 100 ml of an aqueous-alcoholic solution of thioglycolic acid containing 184 g/l (2M). The solvent is composed of 2-propanol dissolved in water in the proportion of 10% by mass. A flow of supercritical $CO_2$ is established by means of the pump 22 under the following extraction conditions:
pressure: $200 \times 10^5$ pascals
temperature: 35° C.
circulation flow rate: 2.1 kg/h
The extraction time is fixed at 20 minutes. After decompression and draining, the aqueous-alcoholic solution no longer has the initial unpleasant odor.

EXAMPLE 6

The autoclave 21 is charged with 100 ml of a solution of thioglycolic acid containing 184 g/l (2M). The solvent is composed of glycerol dissolved in water in the proportion of 3% by mass. The extraction conditions are:

pressure: 200×10⁵ pascals
temperature: 35° C.
circulation flow rate: 2.1 kg/h

An extraction time of 20 minutes provides for a very positive olfactory result: the solution no longer has the initial unpleasant odor.

Examples 7 to 13 relate to applications of solutions of mercaptoacetic acid according to the invention.

EXAMPLE 7

The following are prepared:
A—Reducing composition:
This preparation is made from two solutions stored in different bottles.

| Solution (a) | |
| --- | --- |
| Aqueous solution of deodorized thioglycolic acid containing 36% of active substance | 25 g |
| Solution (b) | |
| Laurylamine oxide marketed by the company "AKZO" under the name "AROMOX DMMCD/W" | 2 g |
| Ethylene diaminetetraacetic acid | 0.15 g |
| Monoethanolamine qs | pH 9.0 |
| Demineralized water qs | 75 g |

After the solution (a) is mixed with the solution (b), a reducing composition having a pH of 9.0 is obtained.

This reducing composition is applied to wet hair previously wound on curlers, the hair is then covered with a plastic bonnet and the composition is left to act for 15 minutes at room temperature. The hair is then rinsed copiously with water and the oxidizing composition defined in B is then applied.

B—An oxidizing composition

| Hydrogen peroxide | 2 g |
| --- | --- |
| Sodium stannate | 0.015 g |
| Ammonium lauryl sulphate | 1.4 g |
| Protein hydrolysate | 0.6 g |
| Citric acid | 0.5 g |
| Perfume qs | |
| Demineralized water qs | 100 g |

The oxidizing composition is left to act for 5 minutes, the hair is then unwound and the composition is left to act for a further 3 minutes. Lastly, the hair is rinsed copiously with water.

After drying under a salon dryer, it is noted that the hair has beautiful locks with a good degree of curling.

The operator's sense of smell failed to detect the development of any nauseating odor during the operation.

EXAMPLE 8

Using the same procedure as that described in Example 7, a permanent-reshaping of hair was carried out using the following reducing and oxidizing compositions:
A—Reducing composition

| Solution (a) | |
| --- | --- |
| Aqueous solution of deodorized thioglycolic acid containing 18% of active substance | 50 g |
| Solution (b) | |
| Laurylamine oxide marketed by the company "AKZO" under the name "AROMOX DMMCD/W" | 0.9 g |
| Diethylenetriaminepentaacetic acid pentasodium salt | 0.15 g |
| Perfume qs | |
| Ammonia solution (20% in water) qs | pH 7.8 |
| Demineralized water qs | 50 g |

On mixing, a composition having a pH of 7.8 is obtained.

B—Oxidizing composition
The same oxidizing composition as that described in Example 7 is used.

The operator's sense of smell failed to detect the development of any nauseating odor during the operation.

EXAMPLE 9

Using the same procedure as that described in Example 7, a permanent-reshaping of hair was carried out using the following reducing and oxidizing compositions:
A—Reducing composition

| Solution (a) | |
| --- | --- |
| Aqueous solution of deodorized thiolactic acid containing 22% of active substance | 50 g |
| Solution (b) | |
| Laurylamine oxide marketed by the company "AKZO" under the name "AROMOX DMMCD/W" | 0.9 g |
| Perfume qs | |
| Ammonia solution (20% in water) qs | pH 8.2 |
| Demineralized water qs | 50 g |

On mixing, a composition having a pH of 8.2 is obtained.

B—Oxidizing composition
The same oxidizing composition as that described in Example 7 is used.

The operator's sense of smell failed to detect the development of any nauseating odor during the operation.

EXAMPLE 10

Using the same procedure as that described in Example 7, a permanent-reshaping of hair was carried out using the following reducing and oxidizing compositions:
A—Reducing composition

| Solution (a) | |
| --- | --- |
| Aqueous solution of deodorized thioglycolic acid containing 18% of active substance | 50 g |
| Solution (b) | |
| Cysteine | 4.5 g |
| Stearic ester polyoxyethylenated with 8 mol of ethylene oxide, marketed by the company "ICI" under the name "MYRJ 45" | 0.85 g |
| Preservative | 0.35 g |
| Perfume qs | |
| Ammonia solution qs | pH 8.8 |
| Demineralized water qs | 50 g |

On mixing, a composition having a pH of 8.8 is obtained.

B—Oxidizing composition

| Hydrogen peroxide (20 volumes) | 40 g |
|---|---|
| Citric acid qs | pH 3.2 |
| Demineralized water qs | 100 g |

The operator's sense of smell failed to detect the development of any nauseating odor during the operation.

EXAMPLE 11

Using the same procedure as that described in Example 7, a permanent-reshaping of hair was carried out using the following reducing and oxidizing compositions:

A—Reducing composition

| Solution (a) | |
|---|---|
| Aqueous solution of deodorized thioglycolic acid containing 18% of active substance | 40 g |
| Solution (b) | |
| Cysteamine hydrochloride | 6.0 g |
| Laurylamine oxide marketed by the company "AKZO" under the name "AROMOX DMMCD/W" | 2 g |
| Preservative | 0.15 g |
| Perfume qs | |
| Monoethanolamine qs | pH 7.8 |
| Demineralized water qs | 60 g |

On mixing, a composition having a pH of 7.8 is obtained.

B—Oxidizing composition

| Sodium bromate | 8 g |
|---|---|
| Triethanolamine qs | pH 8 |
| Monosodium phosphate, hydrated (12H$_2$O) | 0.3 g |
| Trisodium phosphate, hydrated | 0.5 g |
| Cocamidopropylbetaine marketed by the company "GOLDSCHMIDT" under the name "TEGOBETAINE HS" | 1 g |
| Perfume qs | |
| Demineralized water qs | 100 g |

The operator's sense of smell failed to detect the development of any nauseating odor during the operation.

EXAMPLE 12

The following were used:

A—A reducing composition stored in a single bottle and having the following composition:

| Aqueous solution of deodorized thioglycolic acid containing 36% of active substance | 25 g |
|---|---|
| Laurylamine oxide marketed by the company "AKZO" under the name "AROMOX DMMCD/W" | 2 g |
| Ethylenediaminetetraacetic acid | 0.15 g |
| Monoethanolamine qs | pH 9 |
| Demineralized water qs | 100 g |

This reducing composition is applied to wet hair previously wound on curlers, the hair is then covered with a plastic bonnet and the composition is thereafter left to act for 15 minutes at room temperature. The hair is then rinsed copiously with water and the following oxidizing composition is applied:

B—Oxidizing composition

| Hydrogen peroxide | 2 g |
|---|---|
| Sodium stannate | 0.015 g |
| Ammonium lauryl sulphate | 1.4 g |
| Protein hydrolysate | 0.6 g |
| Citric acid | 0.5 g |
| Perfume qs | |
| Demineralized water qs | pH 100 g |

The operator's sense of smell failed to detect the development of any nauseating odor during the operation.

EXAMPLE 13

The following are prepared:

A—A reducing composition for straightening, from two solutions stored in different bottles:

| Solution (a) | |
|---|---|
| Aqueous solution of deodorized thioglycolic acid containing 18% of active substance | 50 g |
| Solution (b) | |
| Polyacrylic acid marketed by the company "GOODRICH" under the name "CARBOPOL 934" | 8 g |
| Ammonia solution (20% in water) qs | pH 8.2 |
| Perfume qs | |
| Demineralized water qs | 50 g |

After the solution (a) is mixed with the solution (b), a reducing composition for straightening, having a pH of 8.2, is obtained.

This composition is applied to wet, initially curly hair, and the hair is stroked using a comb so as to make it straight. After an exposure time of 10 minutes, the hair is rinsed copiously with water and the following oxidizing composition is applied:

B—Oxidizing composition

| Hydrogen peroxide | 2 g |
|---|---|
| Sodium stannate | 0.015 g |
| Ammonium lauryl sulphate | 1.4 g |
| Protein hydrolysate | 0.6 g |
| Citric acid | 0.5 g |
| Perfume qs | |
| Demineralized water qs | 100 g |

The oxidizing composition is left to act for 5 minutes and the hair is then rinsed copiously with water.

The operator's sense of smell failed to detect the development of any nauseating odor during the operation.

EXAMPLE 14

Depilatory composition

The following are prepared:

| Solution (a) | |
|---|---|
| Aqueous solution of deodorized thioglycolic acid containing 18% of active substance | 20 g |
| Solution (b) | |
| Urea | 5 g |
| Calcium carbonate | 1 g |
| Cetyl/stearyl alcohol and oxyethylenate cetyl/stearyl alcohol (80:20 mixture) | 10 g |
| Perfume qs | |
| Demineralized water qs | 80 g |

The solution (a) is mixed with the solution (b) at the time of use, and the pH is adjusted to 11.2 by adding calcium hydroxide.

This composition is applied to the skin and left to act for 10 minutes, and the skin is then rinsed copiously with water.

The operator's sense of smell failed to detect the development of and nauseating odor during the operation.

We claim:

1. A process for deodorizing a mercapto acid by extraction of a greater part of malodorous decomposition products contained therein, said process comprising (a) treating said mercapto acid in the presence of at least one polar solvent for said mercapto acid with a supercritical extraction fluid having a critical temperature ranging from 0° to 135° C. and a critical pressure ranging from $10^6$ to $10^7$ Pascals, said mercapto acid having the formula

HS—A—COOH                                    (I)

wherein
   A represents
   (i) —$(CH_2)_n$— wherein n is an integer ranging from 1 to 4,
   (ii)

wherein R represents linear or branched $C_1$-$C_3$ alkyl, or
   (iii)

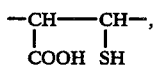

and
   (b) lowering the extraction pressure whereby said malodorous decomposition products are removed with said extraction fluid.

2. The process of claim 1 wherein said supercritical extraction fluid is carbon dioxide.

3. The process of claim 1 wherein said mercapto acid is thioglycolic acid or thiolactic acid.

4. The process of claim 1 wherein said polar solvent is selected from the group consisting of water, a linear or branched $C_1$-$C_5$ monohydric alcohol, a $C_2$-$C_4$ diol, a $C_3$-$C_6$ polyol and a mixture thereof.

5. The process of claim 4 wherein said monohydric alcohol is selected form the group consisting of methanol, ethanol, 1-propanol, 2-propanol, 1-butanol, 2-butanol, 2-methylpropanol and 1-pentanol.

6. The process of claim 4 wherein said diol is selected from the group consisting of ethylene glycol, 1,2-propanediol, 1,3-propanediol, 1,3-butanediol, 2,3-butanediol, 1,5-pentanediol, and 1,6-hexanediol.

7. The process of claim 4 wherein said polyol is glyercol.

8. The process of claim 1 wherein said polar solvent is present in an amount ranging from 1 to 99 percent by weight relative to the weight of said mercapto acid.

9. The process of claim 1 wherein said mercapto acid is present in the form of an aqueous solution having a mercapto acid concentration ranging from 0.1 mol/liter to 14 mols/liter.

10. The process of claim 1 wherein said extraction is performed in the presence of an inert gaseous compound.

11. The process of claim 10 wherein said inert gaseous compound is selected from the group consisting of helium, nitrogen and argon.

12. The process of claim 1, effected in a discontinuous fashion, said process comprising
    (a) introducing into a reactor said mercapto acid, said polar solvent, said extraction fluid and optionally an inert gaseous compound and closing said reactor,
    (b) establishing in said closed reactor said critical temperature and pressure conditions defined in claim 1,
    (c) permitting said mercapto acid, said polar solvent, said extraction fluid and optionally said inert gaseous compound to remain in contact for a period of time ranging from 5 to 30 minutes,
    (d) removing said extraction fluid by decompression,
    (e) optionally repeating steps (a) to (d) under the said critical temperature and pressure conditions defined in claim 1, and
    (f) collecting a solution of deodorized mercapto acid.

13. The process of claim 1, effected in a semi-continuous fashion, said process comprising
    (a) introducing into a reactor said mercapto acid and said polar solvent,
    (b) filling said reactor with said extraction fluid and closing said reactor,
    (c) establishing in said reactor temperature and pressure conditions exceeding the critical temperature and pressure condition defined in claim 1,
    (d) establishing a washing flow of said supercritical extraction fluid and thereafter discontinuing said flow,
    (e) effecting decompression of said reactor and
    (f) collecting deodorized mercapto acid.

14. The process of claim 13 wherein said extraction fluid is carbon dioxide and said washing flow ranges from 0.5 to 3 kg/hour.

15. The process of claim 14 wherein said mercapto acid is thioglycolic acid, said washing flow of carbon dioxide ranges from 1 to 30 kg/hour per kg of thioglycolic acid/polar solvent mixture.

16. The process of claim 1 wherein said extraction is carried out in a continuous fashion in a separating column.

17. The process of claim 12 which includes recycling said extraction fluid subsequent to removal of said malodorous decomposition products.

* * * * *